United States Patent [19]
Holl et al.

[11] Patent Number: 5,554,650
[45] Date of Patent: Sep. 10, 1996

[54] ANTIPHLOGISTIC, ANALGESIC, ANTIPYRETIC INJECTION PREPARATION

[75] Inventors: Richard J. Holl; Thomas R. Tice; Laura L. Williams, all of Birmingham, Ala.

[73] Assignee: Southern Research Institute, Birmingham, Ala.

[21] Appl. No.: 281,579

[22] Filed: Jul. 28, 1994

[51] Int. Cl.$^6$ ................................................ A61K 31/135
[52] U.S. Cl. ............................................................... 514/567
[58] Field of Search ............................................. 514/567

[56] References Cited

U.S. PATENT DOCUMENTS 5,208,035  5/1993  Okuyama et al. ..................... 424/446

FOREIGN PATENT DOCUMENTS

0595766A1  5/1994  European Pat. Off. .
61-072714  4/1986  Japan .
5178763  7/1993  Japan .

OTHER PUBLICATIONS

Engström et al., Liquid Crystalline Phases as Delivery Systems for Drugs I. Basic Principles, Food Technology and Physical Chemistry, Chemical Centre, Lund, Sweden (1988), Process Intern Symp. Rel. Biol. Mater 15.

Lötroth et al., Liquid Crystalline Phases as Delivery Systems for Drugs II. In–Vitro, Department of Physical Pharmacy, AB Hassle, Mölndal, Sweden (1988), Process Intern Symp. Rel. Biol. Mater 15.

Ericsson et al., Liquid Crystalline Phases as Delivery Systems for Drugs II. In–Vivo, S–200 62 Malmö, Sweden (1988), Process Intern Symp. Rel. Biol. Mater 15.

Larsson, Cubic Lipid—Water Phases: Structures and Biomembrane Aspects, J. Phys. Chem. (1989), vol. 93, pp. 7304–7314.

Engström, Drug Delivery From Cubic and other Lipid–Water Phases, Cubic Lipid–Water Phases, 1991.

Hyde et al., A cubic structure consisting of a lipid bilayer forming an infinite periodic minimum surface of the gyroid type in the glycerolmonooleat–water system, Department of Food Technology, University of Lund, Lund, Sweden (1984), Zeitschrift for Kristallographie 163, 213–219.

Michio et al., Solubilization of vitamin K and oils in water by surfactants containing fatty acid triglyceryl esters— Chemical Abstract—105:214097x, 1987.

Gautier et al., Stable microemulsions containing bithionol— Chemical Abstract—111:45291x, 1988.

*Primary Examiner*—Marianne M. Cintins
*Assistant Examiner*—Phyllis G. Spivack
*Attorney, Agent, or Firm*—Pollock, Vande Sande & Priddy

[57] ABSTRACT

An antiphlogistic, analgesic, antipyretic parenteral preparation is disclosed comprising diclofenac, its salt, or both, a surfactant, cosurfactant, water, having a pH of 3–10, and optionally comprising an oily component, that can exhibit sustained therapeutic levels of diclofenac in plasma.

38 Claims, 1 Drawing Sheet

ANTIPHLOGISTIC, ANALGESIC, ANTIPYRETIC INJECTION PREPARATION

TECHNICAL FIELD

The present invention relates to an antiphlogistic, analgesic, antipyretic parenteral preparation, and, in particular, to an antiphlogistic, analgesic, antipyretic parenteral preparation comprising diclofenac, its salt, or both, as effective components. The parenteral preparation of the present invention provides a sustain release of the drug, along with substantial reduction of side effects upon and after administration.

BACKGROUND ART

Diclofenac and its salts possess excellent antiphlogistic, analgesic, antipyretic activities, and are widely used for treating various inflammatory diseases, such as acute and chronic rheumatoid arthritis, osteoarthritis, and the like. They are typically formulated for oral administration, as a suppository, in an ointment, or the like.

For these preparations, however, i.e., oral dosage forms, suppositories, and ointments, the pharmaceutical effects fluctuate due to differences between the amount of drug administered and the amount of drug absorbed by the body. In addition, these preparations require a certain period of time for the active components to exhibit their effects because of a time-lag between the administration and absorption. Therefore, intravenous or intramuscular administration is desirable to obtain immediate antiphlogistic, analgesic, or antipyretic effects in the case of serious symptoms requiring an urgent treatment, e.g., for effecting an anti-inflammatory or analgesic action after an operation or injury, or visceral pain associated with an attack, cancer, or the like.

For these reasons parenteral preparations comprising diclofenac and/or its salt have been developed. These compositions comprise diclofenac, its salt, or both, and an alcohol, such as propylene glycol, benzyl alcohol, or the like, and water. These conventional parenteral preparations containing diclofenac and/or its salt have the following side effects. First, they produce pain at the injection site during injection. Second, they induce side effects, such as precordial anxiety, ague, cold sweat, breathing difficulty, numbness of extremities, and the like, due to the rapid increase in drug concentration in the plasma immediately after the injection. In addition, the therapeutic effect of these conventional injectable preparations lasts for a short period of time because the drug is eliminated from the plasma quickly.

The present inventors, therefore, have developed antiphlogistic, analgesic, antipyretic parenteral preparations comprising diclofenac, its salt, or both, which gives reduced side effects upon parenteral administration. Moreover, these new parenteral preparations sustain the release of the drug to achieve long-lasting therapeutic effects.

SUMMARY OF THE INVENTION

Diclofenac parenteral compositions have been developed by the present inventors that comprise a therapeutically effective amount of diclofenac, and/or pharmaceutically acceptable salt thereof, a surfactant, a cosurfactant, water and having a pH of 3–10. In addition, according to preferred aspects of the present invention, the composition also contains an oily component.

Other objectives, features, and advantages of the invention will hereinafter become more readily apparent from the following description.

DETAILED DESCRIPTION OF THE INVENTION AND PREFERRED EMBODIMENTS

Figure 1:
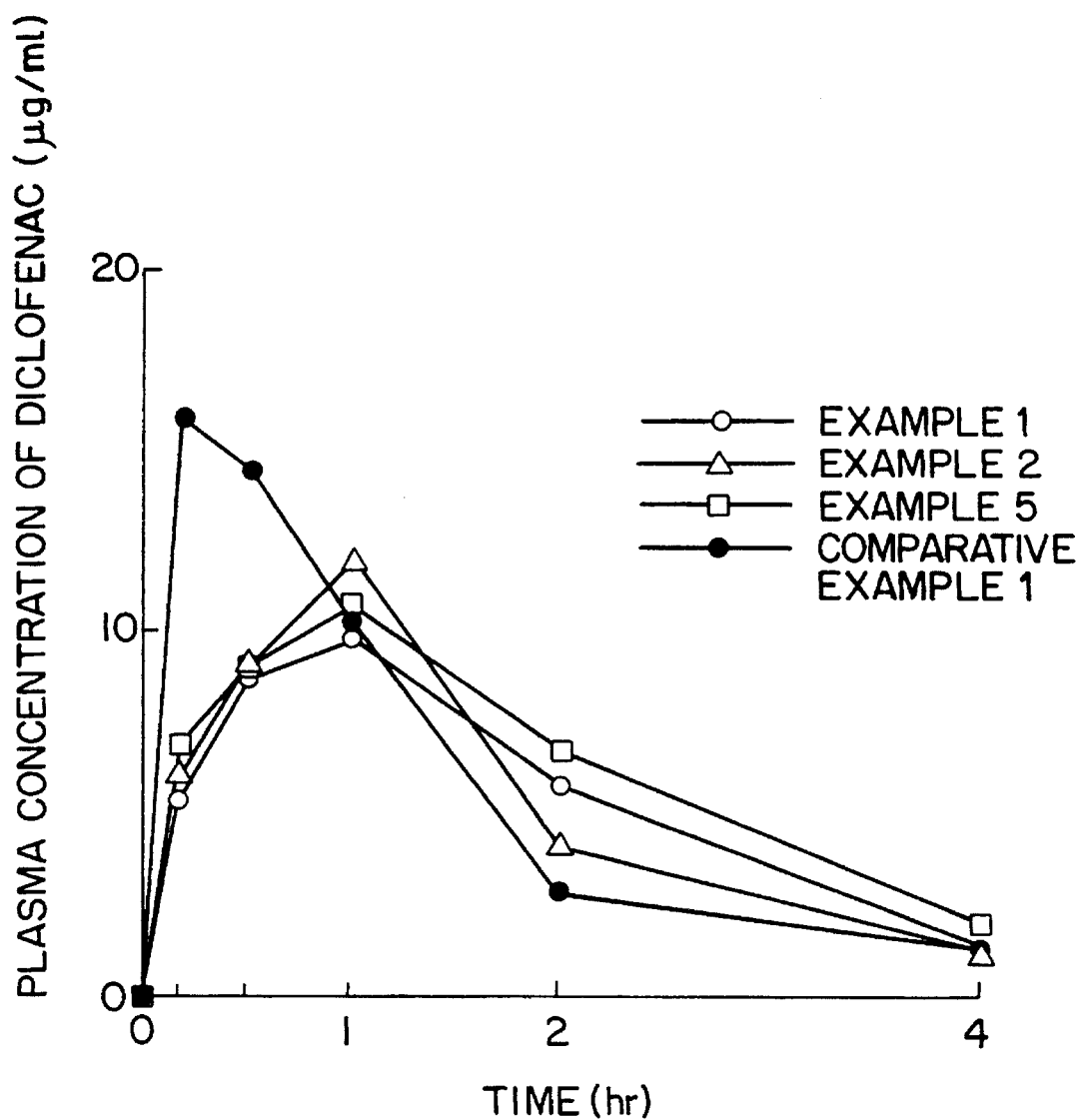
FIG. 1 is a figure showing the plasma profile of diclofenac after intramuscular injection.

Diclofenac used in the parenteral preparation of the present invention as an active component is a compound exhibiting antiphlogistic, analgesic, and antipyretic activities. Its chemical name is 2-(2,6-dichloro-anilino)phenyl acetate. The salts of diclofenac are not specifically limited so long as such salts are pharmaceutically acceptable, and include, for example, alkali metal salts, e.g., sodium salts, potassium salts, etc., ammonium salts, diisopropanol amine salts, and the like. Among these salts, sodium salt is particularly preferred.

The amount of diclofenac and/or its salt to be incorporated in the parenteral preparation is preferably about 2–200 mg/mL, and more preferably about 5–50 mg/mL.

Nonionic surfactants are preferable for use as the surfactant in the present invention. Preferable nonionic surfactants include polyoxyethylene castor oil, polyoxyethylene hydrogenated castor oil, polyoxyethylene sorbitan fatty acid esters, polyoxyethylene alkyl esters, polyoxyethylene alkyl ethers, and sorbitan fatty acid esters. These surfactants can be used either alone or in combination with one more other surfactants. More preferable examples of nonionic surfactants are polyoxyethylene castor oil or polyoxyethylene hydrogenated castor oil with 30–70 moles of ethylene oxide, polyoxyethylene alkyl esters or polyoxyethylene alkyl ethers with 2–40 moles of ethylene oxide, and polyoxyethylene sorbitan fatty acid esters with 5–40 moles of ethylene oxide. Included in particularly preferable nonionic surfactants are polyoxyethylene (40 E.O.) hydrogenated castor oil, polyoxyethylene (60 E.O.) hydrogenated castor oil, polyoxyethylene (20 E.O.) sorbitan monooleate, polyoxyethylene (20 E.O.) sorbitan monopalmitate, and polyoxyethylene (20 E.O.) sorbitan monostearate.

The amount of surfactant(s) in the parenteral preparation of the present invention varies depending on the type(s) of surfactants used. In general, a preferable range is about 2–60 wt %, with the particularly preferable range being about 5–45 wt %.

In the parenteral preparation of the present invention, compounds that function as solubilizers or cosolvents as well as surfactants are preferred. Such compounds can be referred to as cosurfactants. Monohydric or polyhydric alcohols may be used as such cosurfactant either alone or in combination with one or more of the like. Given as examples of monohydric alcohols are benzyl alcohol, ethyl alcohol, and the like; and as examples of polyhydric alcohols are propylene glycol, glycerin, 1,3-butylene glycol, polyethylene glycols with molecular weights of 300–4,000 dalton. Specific examples of such polyethylene glycols include polyethylene glycol 300; polyethylene glycol 400, polyethylene glycol 600, and polyethylene glycol 4,000.

Such a cosurfactant may be incorporated in the parenteral preparation of the present invention in an amount of about 0.5–30 wt %, and preferably 2–15 wt %.

According to preferred aspects of the present invention, such a consurfactant includes benzyl alcohol. The amount of benzyl alcohol is up to about 25 wt %, and preferably less than 25 wt %. When benzyl alcohol is employed the cosurfactant component, the amount of cosurfactant component is about 0.5 wt % to about 25 wt %, preferably about 1 wt % to about 20 wt %, and most preferably about 2 wt % to about 15 wt % of the total composition. When a second cosurfactant is employed with the benzyl alcohol as the cosurfactant component, ethyl alcohol is preferable. The amount of the ethyl alcohol is preferably about 0.5 wt % to about 15 wt % of the total composition. The ethyl alcohol reduces the viscosity of the preparation which makes administration easier.

In addition, benzyl alcohol should be less than about 25 wt %, and preferably about 20 wt % or lower, to prevent undesired reactions with body tissue upon administration.

In addition, according to a further preferred aspect of the present invention, an oily component is employed in the composition. Incorporation of an oily component in the parenteral preparation of the present invention decreases the peak plasma concentration of diclofenac or its salt after administration, increases the time to achieve peak plasma concentration of diclofenac or its salt after administration, and prolongs the period of time for which diclofenac or its salt remains active.

One or more oily components selected from the group consisting of glycerin fatty acid esters, fatty acid esters, and hydrocarbons can be used as the oily component in the present invention. Pharmaceutically acceptable monoglycerides, diglycerides, or triglycerides or their mixtures can be used as the glycerin fatty acid ester, irrespective of their sources or origins, whether they are naturally occurring or synthetic compounds, or semi-synthetic compounds. Given as preferable glycerin fatty acid esters are almond oil, olive oil, sesame oil, peanut oil, fennel oil, camellia oil, corn oil, castor oil, cotton seed oil, and soybean oil, either crude or refined, and medium chain fatty acid triglycerides. They may be used either alone or in combination of one or more oily components. Particularly preferred are cotton seed oil, castor oil, soybean oil, and medium chain fatty acid triglycerides. Isopropyl myristate is preferably used as the fatty acid ester; and light or heavy liquid paraffin as the hydrocarbon. These oily components may be incorporated in the parenteral preparation of the present invention in an amount of about 0.5–30 wt %, preferably 1–15 wt %.

Another essential component of the parenteral preparation of the present invention is water. However, other components, such as preservatives, stabilizers, coloring preventives, soothing agents, isotonic agents, and the like, may be added as needed. The parenteral preparation of the present invention has a pH of 3–10, preferably 3.5–8.0, and more preferably 4.5–7.5. The adjustment of the pH to the above-mentioned range can be accomplished preferably by the addition of a buffering agent. Acetic acid, citric acid, phosphoric acid, and/or their salts are given as examples of preferred buffering agents.

The parenteral preparation of the present invention can be prepared according to a conventional method, for example, dissolving the diclofenac, its salt, or both in a surfactant or in a surfactant/cosurfactant mixture. To aid in the dispersion and dissolution of diclofenac, its salt, or both, surfactants that are paste-like at room temperature can be heated to form a liquid. To this mixture is added, as required, the oily component. Purified water containing a buffering agent, isotonic agents, and the like is added and the mixture is thoroughly stirred. The resulting mixture can then be sterilized, for example, by passing the mixture through a 0.22—μm filter.

The preferred preparations of the present invention are in the form of microemulsions, and most preferably microemulsions of the oil-in-water type. However, microemulsions of the water-in-oil type can also be employed, if desired.

An oil-in-water microemulsion is one in which oil droplets (disperse phase) of 10 to 200 nanometers are dispersed in water (continuous phase). The oil droplets are stabilized by a surfactant and a cosurfactant.

Injection pain is reduced with the preferred microemulsion formulation of diclofenac sodium by two mechanisms. First, the continuous phase of the microemulsion is an isotonic aqueous buffer. This aqueous buffer prevents hypertonic or hypotonic conditions from occurring at the injection site. Hypertonic or hypotonic condition can disrupt the membranes of cells near the injection site and cause pain. When injected, solvents are known to produce a hypotonic effect. For example, the conventional prior-art formulation contains 20% propylene glycol. This propylene glycol may cause injection pain.

Second, the diclofenac is contained within the oil droplets of the microemulsion. Because it takes time for the oil droplets to destabilize and free-up the diclofenac, the diclofenac is released into the bloodstream at a much slower rate than conventional prior-art formulations. This slower release rate prevents diclofenac from precipitating at the injection site. Because the solvent (propylene glycol) of the prior-art conventional formulation disperses rapidly upon injection, diclofenac can precipitate at or near the injection site. The precipitation of the diclofenac can contribute to injection pain.

In addition to the reduction in pain, the microemulsion formulation of diclofenac has an additional benefit. Because of the time it takes for the oil droplets to destabilize, the microemulsion formulation sustains the release of diclofenac and its salts, which maintains effective levels of drug for a longer duration than prior-art preparations.

Another preferred aspect of the present invention is that the preparations can be formulated without the oily component. These formulations are surfactant micelies. These formulations can be filter sterilized and have relatively high drug-loadings and good stability. The size of the droplets of a surfactant micelle can be similar to that of the microemulsion disperse phase, except that the surfactant micelle in many cases is somewhat smaller, such as less than 10 nanometers.

The present invention makes it possible to obtain antiphlogistic, analgesic, antipyretic parenteral preparations that cause no pain upon injection, can avoid occurrence of side effects such as shock which occurs with past diclofenac injectable preparations (due to rapid plasma diclofenac concentration increase immediately after the injection), and displays therapeutic action over an extended period of time.

Other features of the invention will become apparent in the course of the following description of the preferred examples of the present invention, which are given for illustration of the invention and are not intended to be limiting thereof.

EXAMPLES

Example 1:

Polyoxyethylene (60 E.O.) hydrogenated castor oil was melted by heating (about 32 wt % of the final composition).

Soybean oil (about 2 wt % of the final composition) and benzyl alcohol (about 10 wt % of the final composition) were added and mixed. Diclofenac sodium (about 2.44 wt % of the final composition) was added to the resulting solution and dissolved. Then, 2.03 w/v % acetic acid buffer solution (about 53.56 wt % of the final composition) adjusted to pH 4.5 was added to the solution. The mixture was gently mixed, sterilized by filtering it through a membrane filter (0.22—μm filter; manufactured by Millipore Co.), and filled in vials which were sterilized in advance to obtain antiphlogistic, analgesic, antipyretic injection preparation of the present invention. This resultant microemulsion is thermodynamically stable. This microemulsion results from the physical chemistry of the formulation, not from processing it through high-shear equipment.

Example 2:

A parenteral preparation containing about 33 wt % of polyoxyethylene (60 E.O.) hydrogenated castor oil, about 7 wt % of soybean oil, about 10 wt % of benzyl alcohol, about 2.44 wt % of diclofenac sodium and 47.56 wt % of 2.03 w/v % of sodium acetate aqueous buffer was prepared according to the general procedure set forth in Example 1.

Example 3:

A parenteral preparation containing about 19 wt % of polyoxyethylene (40 E.O.) hydrogenated castor oil, about 26 wt % of medium chain fatty acid triglyceride, about 10 wt % of benzyl alcohol, about 2.44 wt % of diclofenac sodium and about 42.56 wt of 2.03 w/v % of sodium acetate aqueous buffer was prepared according to the general procedure set forth in Example 1.

Example 4:

About 35 wt % of polyoxyethylene (20 E.O.) sorbitan monooleate, about 7 wt % of benzyl alcohol, about 2.44 wt % of diclofenac sodium and 55.56 wt % of 2.03 w/v % of sodium acetate aqueous buffer was prepared according to the general procedure set forth in Example 1.

Example 5

A parenteral preparation containing about 35 wt % of polyoxyethylene (60 E.O.) hydrogenated castor oil, about 10 wt % of soybean oil, 10 wt % of benzyl alcohol, about 2.44 wt % of diclofenac sodium and 42.56 wt % of 2.03 w/v % of sodium acetate aqueous buffer was prepared according to the general procedure set forth in Example 1.

Example 6

A parenteral preparation containing about 34 wt % of polyoxyethylene (60 E.O.) hydrogenated castor oil, about 10 wt % of soybean oil, about 10 wt % of benzyl alcohol, about 2.44 wt % of diclofenac sodium and about 43.56 wt % of 2.03 w/v % of sodium acetate aqueous buffer was prepared according to the general procedure set forth in Example 1.

Example 7

A parenteral preparation containing about 32 wt % of polyoxyethylene (60 E.O.) hydrogenated castor oil, about 2 wt % of soybean oil, 10 wt % of benzyl alcohol, about 0.98 wt % of diclofenac sodium and about 55.02 wt % of 2.03 w/v % of sodium acetate aqueous buffer was prepared according to the general procedure set forth in Example 1.

Example 8

A parenteral preparation containing about 26 wt % of polyoxyethylene (40 E.O.) hydrogenated castor oil, about 19 wt % of medium chain fatty acid triglyceride, about 10 wt % of benzyl alcohol, 2.44 wt % of diclofenac sodium and about 42.56 wt % of sodium acetate aqueous buffer was prepared according to the general procedure set forth in Example 1.

Example 9

A parenteral preparation containing about 32 wt % of polyoxyethylene (40 E.O.) hydrogenated castor oil, about 13 wt % of medium chain fatty acid triglyceride, about 10 wt % of benzyl alcohol, about 2.44 wt % of diclofenac sodium and about 42.56 wt % of 2.03 w/v % of sodium acetate aqueous buffer was prepared according to the general procedure set forth in Example 1.

Example 10

A parenteral preparation containing about 30 wt % of polyoxyethylene (60 E.O.) hydrogenated castor oil, about 15 wt % of medium chain fatty acid triglyceride, about 10 wt % of benzyl alcohol, about 2.44 wt % of diclofenac sodium and about 42.56 wt % of 2.03 w/v % of sodium acetate aqueous buffer was prepared according to the general procedure set forth in Example 1.

Example 11

Polyoxyethylene (60 E.O.) hydrogenated castor oil (33 wt % of the final composition) was heated and benzyl alcohol (about 10 wt %) was added and mixed. Diclofenac sodium (about 1.46 wt %) was dissolved in the mixture and soybean oil (about 7 wt %) was added and mixed. Sodium acetate aqueous buffer (about 48.54 wt % of 2.03 w/v %) was added. The mixture was processed using a homogenizer to obtain a parenteral preparation.

Example 12

A parenteral preparation having a pH of about 4.5 and containing about 27.31 wt % of polyoxyethylene (60 E.O.) hydrogenated castor oil, about 1.02 wt % of soybean oil, about 10.16 wt % of benzyl alcohol, about 2.53 wt % of ethanol, about 2.44 wt % of diclofenac sodium, and about 56.54 wt % of a 0.69 wt % of sodium acetate aqueous buffer composition was prepared according to the general procedure set forth in Example 1.

Comparative Example 1

To a heated mixture of 20 mL of propylene glycol and 4 mL of benzyl alcohol, 2.5 g of diclofenac sodium was added to dissolve. Purified water, with its osmotic pressure adjusted with mannitol, was added to the solution to make the total volume 100 mL. The preparation contained 25 mg/mL of diclofenac sodium.

Test Example 1

The antiphlogistic, analgesic, antipyretic parenteral preparations of the present invention, prepared in Examples 1, 2, and 5, each containing about 25 mg/mL of diclofenac sodium, and the parenteral preparation containing 25 mg/mL of diclofenac sodium prepared in Comparative Example 1 were intramuscularly injected into hind-legs of SD rats (age: 8 weeks) at a dose of 10 mg/kg. A specified period of time thereafter, 0.2 mL of blood was collected from the eyegrounds to quantify the diclofenac concentration in the plasma by HPLC.

The results are shown in FIG. 1. It is clear that the Comparative Example 1 of diclofenac releases drug quickly in the blood, because of the high peak levels early on. Whereas the preparations of Examples 1, 2, and 5 did not show high peak levels early on. Furthermore, these preparations maintained thereafter a suitable concentration of drug for an extended time, thus avoiding any shocks due to an initial high concentration. In addition to the changes in the diclofenac concentration in blood, the area-under-curve (AUC) of the diclofenac concentration was calculated. As shown in Table i, the antiphlogistic, analgesic, antipyretic parenteral preparations of the present invention obtained in Examples 1, 2, and 5, which contain about 25 mg/mL diclofenac sodium, exhibited the same AUC as Comparative Example 1. These results show that diclofenac sodium is released from the injection preparations of the present invention in a sustained manner without lowering the AUC, reducing the risks of side effects due to a rapid increase in diclofenac concentration in plasma after injection, and extend the duration of drug in the blood.

TABLE 1

| Preparation | $AUC_{0 \to \infty}$ (μg · hr/mL) |
| --- | --- |
| Example 1 | 24.0 |
| Example 2 | 26.7 |
| Example 5 | 31.6 |
| Comparative Example 1 | 27.6 |

Obviously, numerous modifications and variations of the present invention are possible, in light of the above teachings. It is therefore to be understood that within the scope of the appended claims, the invention may be practiced otherwise than as specifically described herein.

What is claimed is:

1. An antiphlogistic, analgesic and antipyretic parenteral preparation comprising a therapeutically effective amount of diclofenac, its pharmaceutically acceptable salt, or both, a surfactant, a cosurfactant, and water, and having a pH of 3–10.

2. The parenteral preparation according to claim 1, wherein said surfactant is a nonionic surface active agent.

3. The parenteral preparation according to claim 1, wherein said surfactant is one or more compounds selected from the group consisting of polyoxyethylene castor oil, polyoxyethylene hydrogenated castor oil, polyoxyethylene sorbitan fatty acid esters, sorbitan fatty acid esters, polyoxyethylene alkyl esters, and polyoxyethylene alkyl ethers.

4. The parenteral preparation according to claim 1, wherein said cosurfactant is one or more compounds selected from the group consisting of monohydric alcohols and polyhydric alcohols.

5. The parenteral preparation according to claim 1, wherein said cosurfactant is one or more compounds selected from the group consisting of benzyl alcohol, ethyl alcohol, propylene glycol, glycerin, 1,3-butylene glycol, polyethylene glycols with a molecular weight of 300 to 4,000 dalton.

6. The parenteral preparation according to claim 1, wherein said cosurfactant is one or more compounds selected from the group consisting of benzyl alcohol, propylene glycol, and ethyl alcohol.

7. The parenteral preparation according to claim 1, wherein the pH is adjusted by a buffering agent.

8. The parenteral preparation according to claim 1, wherein the pH is adjusted by one or more compounds selected from the group consisting of acetic acid, citric acid, or phosphoric acid, or the salts thereof.

9. The parenteral preparation according to claim 1, comprising 2–200 mg/mL or diclofenac, its salt, or both, 2–60 wt % of a surfactant, and 0.5–30 wt % of a cosurfactant.

10. The parenteral preparation according to claim 1, comprising 5–50 mg/mL of diclofenac, its salt, or both, 5–45 wt % of a surfactant, and 2–15 wt % of a cosurfactant.

11. An antiphlogistic, analgesic, antipyretic parenteral preparation comprising diclofenac, its salt, or both, a surfactant, a cosurfactant, an oily components, and water, and having a pH of 3–10.

12. The parenteral preparation according to claim 11, wherein said oily component is one or more compounds selected from the group consisting of glycerin fatty acid esters, fatty acid esters, and hydrocarbons selected from the group consisting of light liquid paraffin and heavy liquid paraffin.

13. The parenteral preparation according to claim 11, wherein said oily component is one or more compounds selected from the group consisting of cotton seed oil, castor oil, soybean oil, medium chain fatty acid triglycerides, isopropyl myristate, and liquid paraffin.

14. The parenteral preparation according to claim 11, wherein said surfactant is a nonionic surface active agent.

15. The parenteral preparation according to claim 11, wherein said surfactant is one or more compounds selected from the group consisting of polyoxyethylene castor oil, polyoxyethylene hydrogenated castor oil, polyoxyethylene sorbitan fatty acid esters, sorbitan fatty acid esters, polyoxyethylene alkyl esters, and polyoxyethylene alkyl ethers.

16. The parenteral preparation according to claim 11, wherein said cosurfactant is one or more compounds selected from the group consisting of monohydric alcohols and polyhydric alcohols.

17. The parenteral preparation according to claim 11, wherein said cosurfactant is one or more compounds selected from the group consisting of benzyl alcohol, ethyl alcohol, propylene glycol, glycerin, 1,3-butylene glycol, polyethylene glycols with a molecular weight of 300 to 4,000 dalton.

18. The parenteral preparation according to claim 11, wherein said cosurfactant is one or more compounds selected from the group consisting of benzyl alcohol, propylene glycol, and ethyl alcohol.

19. The preparation of claim 18 wherein the benzyl alcohol is about 0.5 to about 25% by weight.

20. The preparation of claim 18 wherein the benzyl alcohol is about 1 to about 20 wt %.

21. The preparation of claim 18 wherein the amount of said ethyl alcohol is about 0.5 to about 15 wt % of the preparation, and the amount of said benzyl alcohol is about 0.5 to about 20 wt %.

22. The parenteral preparation according to claim 11, wherein the pH is adjusted by a buffering agent.

23. The parenteral preparation according to claim 11, wherein the pH is adjusted by one or more compounds selected from the group consisting of acetic acid, citric acid, or phosphoric acid, or the salts thereof.

24. The parenteral preparation according to claim 11, comprising 2–200 mg/mL of diclofenac, its salt, or both, 2–60 wt % of a surfactant, 0.5–30 wt % of a cosurfactant, and 0.5–30 wt % of an oily component.

25. The parenteral preparation according to claim 11, comprising 5–50 mg/mL of diclofenac, its salt, or both, 5–45 wt % of a surfactant, 2–15 wt % of a cosurfactant, and 1–15 wt % of an oily component.

26. An antiphlogistic, analgesic, antipyretic parenteral microemulsion preparation comprising of diclofenac, its salt, or both; a surfactant and a cosurfactant, wherein the amount of said cosurfactant is about 0.5 to 30 wt % of the preparation, an oily component, and water, and having a pH of 3–10.

27. The preparation of claim 26 wherein the amount of said cosurfactant is about 1 to about 20 wt %.

28. The preparation of claim 26 wherein the amount of said cosurfactant is about 2 to about 15% by weight.

29. The preparation of claim 26 wherein said cosurfactant also contains ethyl alcohol.

30. The parenteral preparation according to claim 26, wherein said oily component is one or more compounds selected from the group consisting of glycerin fatty acid esters, fatty acid esters, and hydrocarbons selected from the group consisting of light liquid paraffin and heavy liquid paraffin.

31. The parenteral preparation according to claim 26, wherein said oily component is one or more compounds selected from the group consisting of cotton seed oil, castor oil, soybean oil, medium chain fatty acid triglycerides, isopropyl myristate, and liquid paraffin.

32. The parenteral preparation according to claim 26, wherein said surfactant is a nonionic surface active agent.

33. The parenteral preparation according to claim 26, wherein said surfactant is one or more compounds selected from the group consisting of polyoxyethylene castor oil, polyoxyethylene hydrogenated castor oil, polyoxyethylene sorbitan fatty acid esters, sorbitan fatty acid esters, polyoxyethylene alkyl esters, and polyoxyethylene alkyl ethers.

34. The parenteral preparation according to claim 26, wherein the pH has been adjusted by buffering agent.

35. The parenteral preparation according to claim 26, wherein the pH has been adjusted by one or more compounds selected from the group consisting of acetic acid, citric acid, or phosphoric acid, or the salts thereof.

36. The parenteral preparation according to claim 26, comprising 2–200 mg/mL of diclofenac, its salt, or both, 2–60 wt % of a surfactant, and 0.5–30 wt % of an oily component.

37. The parenteral preparation according to claim 26, comprising 5–50 mg/mL of diclofenac, its salt, or both, 5–45 wt % of a surfactant, 1–15 wt % of an oily component.

38. A method for treating a patient in need of an antiphlogistic agent, analgesic or antipyretic agent, which comprises administering to said patient a preparation according to claim 1 by parenteral administration.

* * * * *